US006090347A

United States Patent [19]

Emödi

[11] Patent Number: 6,090,347

[45] Date of Patent: Jul. 18, 2000

[54] TEST KIT AND USE THEREOF

[75] Inventor: Gabriel Emödi, Basel, Switzerland

[73] Assignee: Intex Pharmaceutische Produkte AG, Muttenz, Switzerland

[21] Appl. No.: 09/142,381

[22] PCT Filed: Mar. 21, 1997

[86] PCT No.: PCT/CH97/00121

§ 371 Date: Sep. 4, 1998

§ 102(e) Date: Sep. 4, 1998

[87] PCT Pub. No.: WO97/35663

PCT Pub. Date: Oct. 2, 1997

[30] Foreign Application Priority Data

Mar. 22, 1996 [CH] Switzerland ............................ 0757/96

[51] Int. Cl.[7] .......................... G01N 31/22; G01N 15/06; B01L 9/00; C01B 6/00; C12M 1/00

[52] U.S. Cl. ............................ 422/61; 422/68.1; 422/58; 422/104; 422/162; 436/541; 436/183; 436/513; 435/287.1; 435/287.6; 435/288.2; 435/288.5; 206/469; 206/532; 206/569

[58] Field of Search ............................ 422/61, 68.1, 104, 422/162, 58; 436/541, 808, 183, 513, 809; 435/810, 970, 287.1, 287.6, 288.2, 288.5; 206/469, 532, 569

[56] References Cited

U.S. PATENT DOCUMENTS

| | | | |
|---|---|---|---|
| 3,660,033 | 5/1972 | Schwartz | 23/230 |
| 4,065,263 | 12/1977 | Woodbridge, III | 23/252 |
| 4,343,709 | 8/1982 | Okumura | 210/782 |
| 4,459,710 | 7/1984 | Keyes et al. | 4/227 |
| 4,503,864 | 3/1985 | Powers | 128/760 |
| 4,790,833 | 12/1988 | Schmidt | 604/317 |
| 4,913,161 | 4/1990 | Villari et al. | 128/766 |
| 4,965,047 | 10/1990 | Hammond | 422/58 |
| 5,087,251 | 2/1992 | Heyman et al. | 604/327 |
| 5,263,946 | 11/1993 | Klug | 604/327 |
| 5,354,538 | 10/1994 | Bunce et al. | 422/100 |
| 5,422,271 | 6/1995 | Chen et al. | 435/287 |
| 5,643,236 | 7/1997 | Hadley | 604/327 |
| 5,731,212 | 3/1998 | Gavin et al. | 436/526 |
| 5,770,441 | 10/1996 | Lipton | 435/289 |
| 5,811,296 | 12/1996 | Chemelli et al. | 435/287.2 |
| 5,842,326 | 6/1994 | Wolf | 53/425 |
| 5,843,793 | 10/1995 | Belly et al. | 436/514 |
| 5,846,488 | 12/1998 | Richardson | 422/61 |
| 5,888,832 | 3/1999 | Richardson | 436/183 |

FOREIGN PATENT DOCUMENTS

| | | |
|---|---|---|
| 0 139 373 | 8/1984 | European Pat. Off. . |
| WO 91/16086 | 10/1991 | WIPO . |
| WO 93/07474 | 4/1993 | WIPO . |

*Primary Examiner*—Christopher L. Chin
*Assistant Examiner*—Pensee T. Do
*Attorney, Agent, or Firm*—Leydig, Voit & Mayer

[57] ABSTRACT

The test kit includes a substrate and, welded or bonded thereto, a plastic sheet having blisters. One of the blisters is shaped as a siphon. The other blisters act as reaction vessels and also serve to receive and store a reagent. The test kit may contain a test strip in one of the blisters. The test kit is particularly suited for carrying out immunological tests, whereby the siphon markedly facilitates the procedure during the washing step.

20 Claims, 3 Drawing Sheets

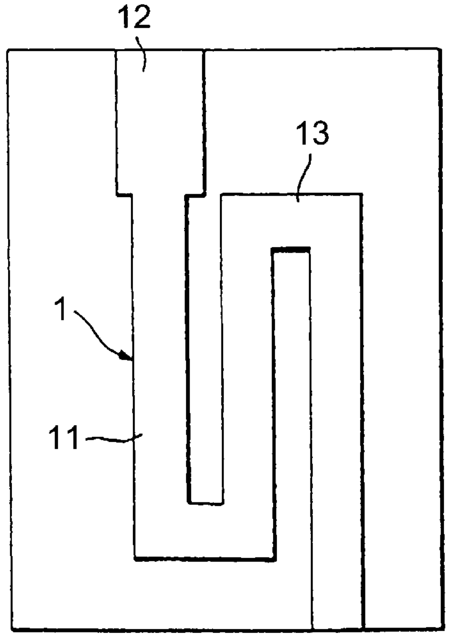
FIG. 1
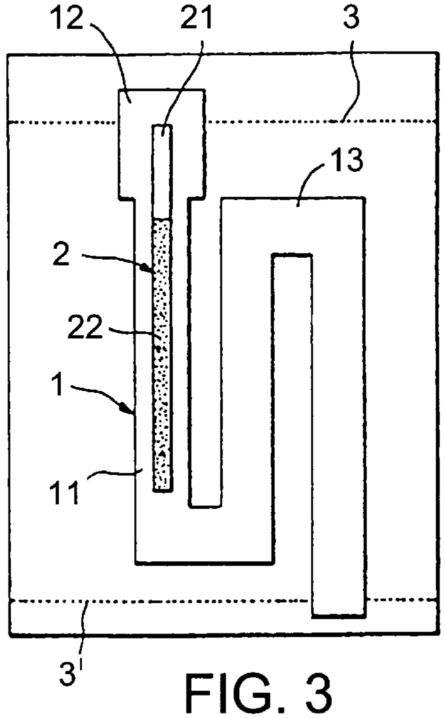
FIG. 3
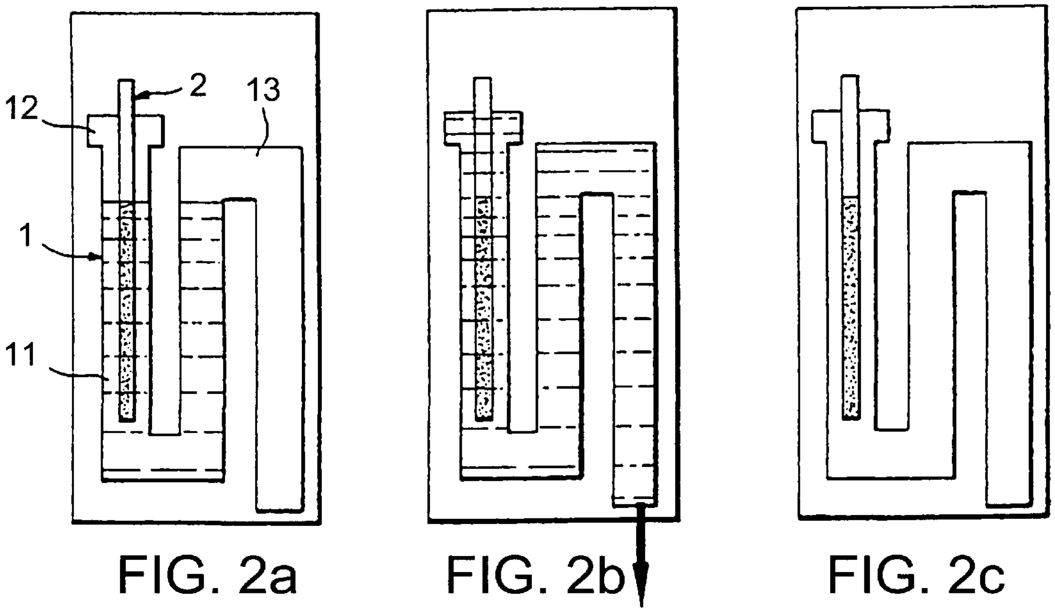
FIG. 2a
FIG. 2b
FIG. 2c

TEST KIT AND USE THEREOF

AREA OF THE INVENTION

The present invention relates to test kits with test vessels which are formed by appropriate shaping of a plastic sheet and welding of this shaped sheet to a substrate, and to the use thereof for carrying out analytical tests, in particular immunological tests.

Vessels which are formed, as described above, by shaping a plastic sheet and welding this sheet to a substrate are referred to as "blisters" in the art. The blister technique is used in particular for packaging tablets or pills of all types. However, it is also employed for packing biological and technical products; thus, for example, flower bulbs or screws are blister-packed.

PRIOR ART

The blister technique has already been employed in analysis for carrying out tests of various types. In the literature on such tests, the blisters are referred to not by their modern name but as bags, envelopes and the like.

Thus, according to FR 2 351 022 (R. Boutroy), elongate bags are formed from two plastic sheets which are welded together; the bags taper to a point at the lower end and are left open at the upper end. After introduction of, for example, a serum sample, the opening is heat-sealed. To remove the sample, the point is cut through or slit open at the side. The bags are intended to be used for storage, centrifugation or transport of samples.

U.S. Pat. No. 3,660,033 (L. L. Schwartz) describes a flexible polyethylene bag for analysis of, for example, a urine sample. The bag comprises successively a sample entrance, a reservoir which can be sealed with respect to the former, and a reaction chamber which contains a reagent for the sample and is connected to the reservoir by a narrow, sealable channel. Part of the sample passes from the reservoir into the reaction chamber, and the remainder can be stored or used for other tests; for this purpose, the connection orifices are closed and the reservoir is detached along the cut lines.

The Patent Application WO 91/16086 (Target Research Inc.) describes a transparent plastic bag for the analysis of physiological fluids. The edge on the upper half of the bag is open for introducing samples; the lower half is formed into a plurality of compartments which are open on the upper half but sealable, and taper at the lower end to a point which can be cut through, and can be detached singly along the welding lines. The compartments, which are arranged on at least one of the halves of the bag, receive individual samples, which are brought into contact with chemical reagents.

Many analytical tests make use of a test strip which contains agents necessary for the test on porous material (for example cellulose, nitrocellulose). During some test methods, the test strip must be washed one or more times with washing solution.

EP 0 139 373 (The Regents of the University of California) describes a test kit inter alia for an ELISA test (Enzyme-Linked Immuno Sorbent Assay). This test kit does not, however, use the blister technique. It consists of a test strip in the form of a column which is composed of several layers of, for example, filter paper or plastic and which is located in a glass tube which is open at both ends. One or more layers of the column carry a reagent bound thereto, in particular a known antigen or the corresponding antibody; they are kept at a distance apart by inert separating layers. The solution to be tested, as well as possible washing solutions, are sucked into the tube by applying a vacuum to the upper end of the tube. The solutions are removed from the tube by applying a superatmospheric pressure.

The Patent Application WO 93/07474 (Hawaii Chemtect International) describes an analytical kit for testing foodstuffs, in particular for detecting fish toxins. It comprises a stiff but flexible, non-porous, preferably water-resistant substrate to which a transparent plastic sheet which is shaped to blisters is affixed. The blisters contain liquid reagents. Half way along, the sheet and substrate have a bending line which also runs through the upper part of the blisters. If the kit is bent back along this line, it assumes the shape of a gable roof and can thus be used standing upright; at the same time, this opens the blisters at their upper ends, and the contained reagents become accessible for the intended reaction. Blisters are provided to the side of the bending line and contain the test strips necessary for the detection. For washing the test strips, a blister referred to as the "washing compartment" is disclosed and has the same structure as the reaction blisters.

In general, investigations with a test strip show that the washing step is problematical because the sample and possible other test solutions penetrate into the pores of the porous carrier material during the incubation. A single wash of the test strip with washing liquid or immersion in the washing liquid does not suffice to remove the unbound material. The washing method described in EP 0 139 373 permits, by pulsatile vacuum, the washing solution to flow on and off the test strip several times, but is technically elaborate. The washing compartment from WO 93/07474 allows only washing of the test strip by static incubation in washing solution, and to change the washing solution it would be necessary to empty out the entire analytical kit, including the reaction blisters with reaction solutions.

The object is thus to find a simple test kit based on the blister technique for tests with a test strip, the intention being with this test kit that two variants of the washing of the test strip be possible, the flowing of the washing solution for its continuous replacement as well as incubation of the test strip in the washing medium to allow diffusion into the pores.

DESCRIPTION OF THE INVENTION

The object is achieved according to the invention by a test kit consisting of a water-impermeable substrate and, bonded or welded thereto, a transparent plastic sheet which is shaped to one or more blisters arranged parallel to one another, this test kit being characterized in that one blister is shaped so that it is able to act as a siphon.

Suitable for the transparent plastic sheet from which the blisters are formed are, inter alia, polystyrene, polyvinyl chloride, polyvinyl carbonate or polyethylene. The material of the sheet advantageously consists of plastic which is hydrophobic or has been made hydrophobic, in order to facilitate introduction of the solutions.

The shaping of the sheet to blisters depends on the intended use of the test kit. For example, the blisters can act as containers of an unused test strip before the reaction or for storing the used test strip as proof after the reaction, as it were for archiving the test strip; in the latter case, they preferably have an elongate shape. If the blisters contain a reaction component present in solid form, for example a sodium bicarbonate pill as buffer substance, they may have, at least for the part intended as container, a circular shape or a shape other than the elongate one already mentioned.

The material of which the substrate consists is water-impermeable. The impermeability to water derives from the fact that, in most cases, the solutions contained in the blisters are aqueous solutions, or the reactions take place in water or in an aqueous medium. Examples of the material of the substrate are aluminium sheet, plastics such as, for example, PVC, and plasticized paper or board. These materials are opaque to light, which is probably the more usual case; however, opacity to light is not an obligatory feature of the substrate characteristics.

The substrate may have, in particular, a quadrilateral shape.

The substrate and the sheet can, where appropriate, consist of the same material, but in any event the materials thereof should be chosen so that they can be welded and/or bonded together and form a leakproof connection on welding or bonding.

The test kit according to the invention is produced (shaping of the sheet and connection to the substrate) by known processes; see, for example, the textbook "Verpacken mit Kunststoffen" [Packaging with Plastics] by Gunther K ühne, Verlag Carl Hanser, Munich 1974.

The test kit according to the invention is especially suitable for carrying out analytical tests with test strips in, for example, chemistry, clinical chemistry, enzymology, molecular biology, cell biology and, in particular, immunology.

The blister acting as a siphon is referred to hereinafter as the siphon blister, and the blisters intended for reactions are called reaction blisters hereinafter.

EXPLANATION OF THE FIGURES

FIG. 1 shows a test kit according to the invention with precisely just one siphon blister 1 which is open at both ends.

FIGS. 2*a*, 2*b* and 2*c* illustrate the washing method carried out on a test strip in the siphon blister 1.

FIG. 3 shows a test kit according to the invention in which the siphon blister 1 is closed before the test and is used for preceding storage of one or more test strips 2.

DESCRIPTION OF PREFERRED EMBODIMENTS

Figure 4:
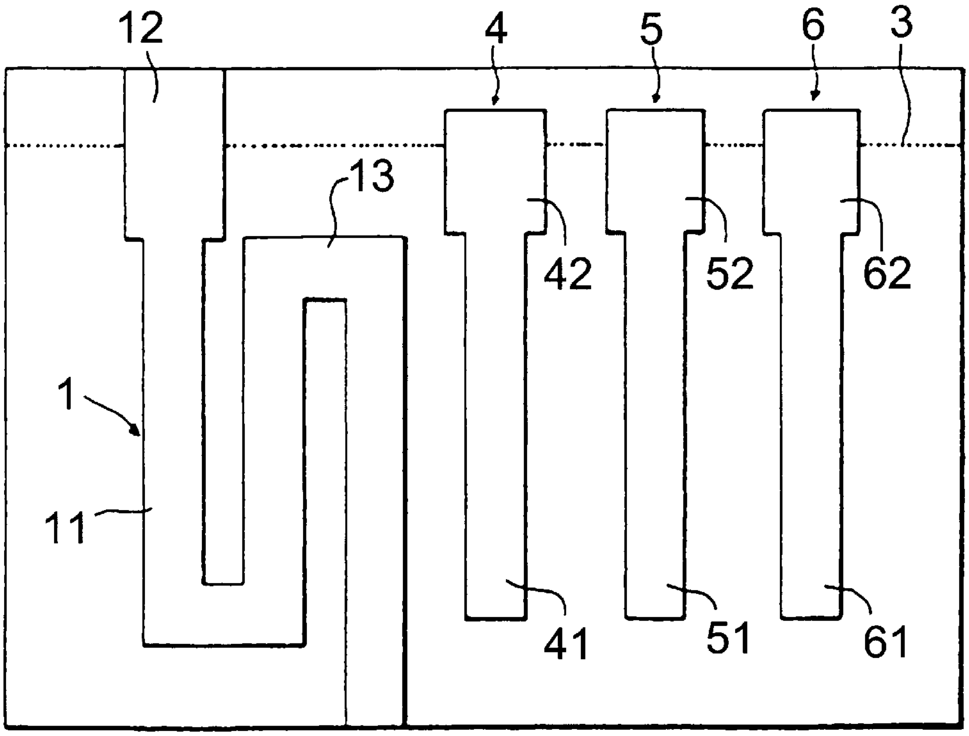
FIG. 4 shows a test kit according to the invention with a siphon blister 1 and three reaction blisters 3, 4 and 5, with the siphon blister being open and the reaction blisters being closed.

In a first embodiment of the invention (FIG. 1), the kit comprises precisely just the one siphon blister 1 which is open at both ends. Its upward-pointing branch consists of a container part 11 and, adjoining at the top, a removal part 12 (whose cross-section may be increased by comparison with that of the container part in order to facilitate manipulation of test strips). The elongate, shallow container part 11 of the siphon blister 1 is extended and curved in an S shape by a rinsing part 13 at the end opposite to the removal part 12, so that container part 11 and rinsing part 13 together form a siphon. The siphon blister is shown in a form open at the removal part 12 and at the end of the rinsing part 13, because in this case it is mostly used only for carrying out the washing step and thus sterility of the siphon blister is unnecessary. For the washing (FIGS. 2*a*, 2*b*, 2*c*), the test strip 2 is introduced into the container part 11 and, with the container part 11 in at least approximately vertical alignment, washing solution is added and can then flow out again through the rinsing part 13. The washing of the test strip 2 takes place with the washing solution either flowing through or stationary, and in the latter case the amount of washing solution initially introduced into the container part 11 is such that no solution escapes through the rinsing part 13 (FIG. 2*a*). Then, in a second step, further washing solution (FIG. 2*b*) is introduced to empty the siphon (FIG. 2c) through the siphon effect. This washing method can be applied to all embodiments of the test kit according to the invention.

The siphon blister can, of course, also be used initially for carrying out a reaction by introducing a reagent solution and immersing a test strip therein.

In a second embodiment of the test kit according to the invention (FIG. 3), likewise precisely just one siphon blister 1 is provided. However, it is now used simultaneously for storing one or more test strips 2 before the test and is initially closed. In the production of this test kit, in analogy to the blister packing of other products, the test kit or kits is/are placed in the preshaped sheet and the latter is only then connected to the substrate.

The test strip 2 consists, for example, of a plastic strip 21 which is long enough for it to extend beyond the end of the container part 11 into the removal part 12, and onto one side of which is applied, at least in part, an absorbent material 22, for example cellulose, nitrocellulose or very fine glass wool. The antibodies; antigens or other types of reactants required for the particular test are arranged thereon, it being possible to form one or more test areas.

In order to be able to act as a siphon in the actual test, both ends of the siphon blister are cut through. To carry out a reaction in the siphon blister, it is also possible first to open only its upward-pointing branch. In order to facilitate cutting through the siphon blister, the test kit can be preperforated along lines 3, 3' located at the upper and lower ends, respectively, of the test kit.

Figure 5A:
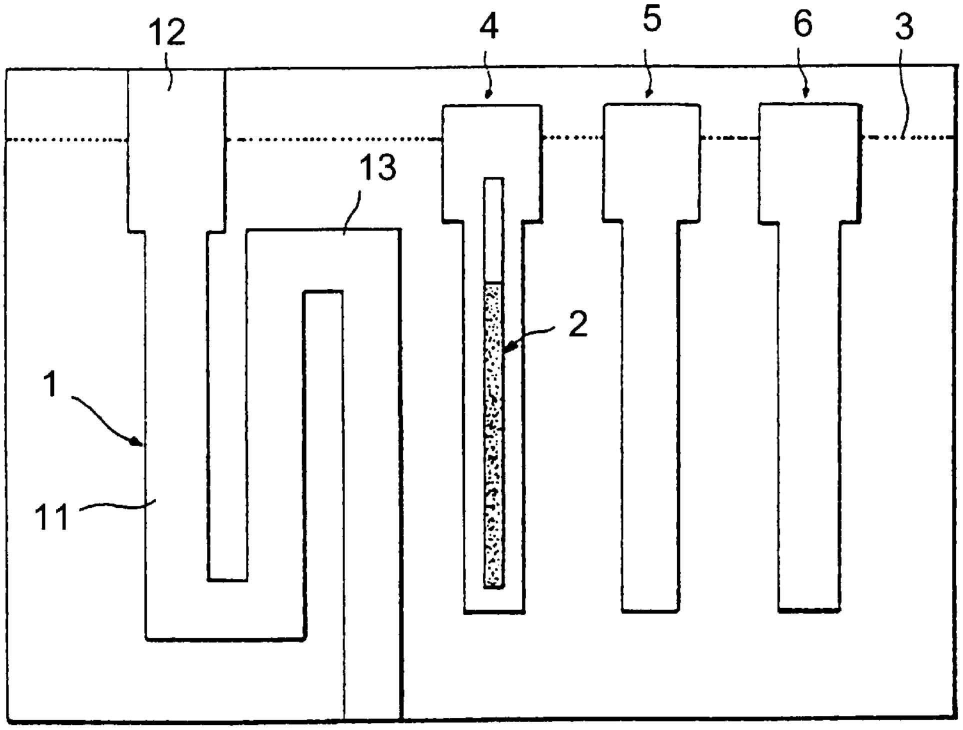
FIGS. 5*a* and 5*b* show test kits according to the invention in which test strips 2 are stored in one of the reaction blisters, and the siphon blister is already open (FIG. 5*a*), or one or more test strips 2 are stored in the siphon blister 1 which is still closed (FIG. 5*b*).
Figure 5B:
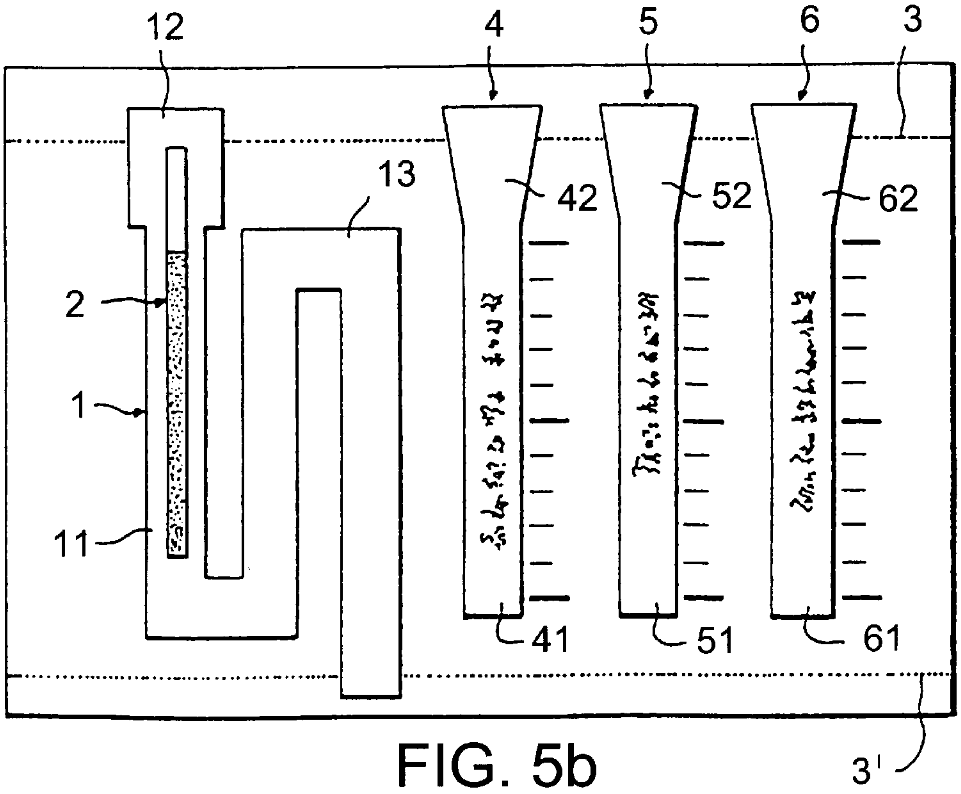

In a third embodiment of the test kit according to the invention (FIG. 4), closed reaction blisters 4, 5, 6 are arranged beside the container part 11 of the siphon blister 1. Each of them consists of a shallow reaction part 41, 51, 61 and an introduction part 42, 52, 62 with a cross-section which is increased by comparison with the reaction part 41, 51, 61. The introduction part 42, 52, 62 makes it possible to introduce the test strip 2 by hand into the reaction part 41, 51, 61 and remove it again therefrom. It is advantageous for it to be funnel-shaped to facilitate introduction of reagents. The introduction parts 42, 52, 62 of the reaction blisters and the introduction part 12 of the siphon blister are preferably side by side and can be cut through along a single line. The line can be marked on the test kit by a preperforated line 3. The reaction blisters 4, 5, 6 can be provided with printed numbers in the region of the introduction parts 42, 52, 62, and volumetric measuring scales can be printed beside them or on them in the region of the reaction parts 41, 51, 61 and can be used to determine the level of filling of the reaction blisters 4, 5, 6. The reaction blisters can be used before the test for storing solid or liquid test reagents. Any test strips which are required can alternatively either be stored in one of the reaction blisters 4, 5, 6 (FIG. 5*a*), or they can be stored in the siphon blister, which is then preferably closed initially (FIG. 5*b*). An embodiment in which at least one of the blisters contains a test strip is preferred.

The particularly preferred embodiment is shown in FIG. 5*b*. The siphon blister 1 is initially the storage container for one or more test strips and is closed. The sheet shaped to blisters consists of polyvinyl chloride and the substrate consists of an aluminium sheet. Sheet and substrate are bonded with adhesive customary in the blister technique. Solid or liquid reagents can be stored in the reaction blisters 4, 5, 6. The reaction parts 41, 51, 61 are volumetrically calibrated with measurement scales (for example in microliter units) and have inscriptions which identify any reagents stored therein or assign the reaction blister to a particular reaction step in the test. The introduction parts 42, 52, 62 are funnel-shaped. The test kit has an inscription area on which the nature of the sample and, for example, the date of the test can be noted. To carry out the test, the test kit is cut through or broken open along a preperforated line 3. The siphon blister can, because it is open only at the top, now serve as reaction blister. In order for it to be able to act as a siphon, the test kit is also cut through along a preperforated line 3'. After the test has been carried out, the test strip can, for example, be stored in the siphon blister which has been completely emptied by the siphon effect.

The invention also relates to the use of the test kit for an analytical test from immunology, especially for an ELISA test.

Immunological tests are based on the fundamental reaction of an antigen with its antibody. For the ELISA technique (Enzyme-Linked immuno Sorbent Assay), one of these reactants (antigen or antibody) is bound to a test strip. The analyte present in the sample is then bound by an immunological reaction to this reactant adsorbed on the test strip. The unbound material is removed in a washing step.

To remove unbound material after the immunological reaction, the test strip is introduced into the blister siphon of the test kit according to the invention and washed with the washing medium flowing through or incubated in the stationary washing solution. It is possible to choose an embodiment of the test kit with precisely only one siphon blister in which case the test reactions are carried out in separate sample containers. However, an embodiment which also comprises reaction blisters is advantageously chosen.

To detect the antigen-antibody reaction, another immunological reagent which reacts with the analyte is added at the same time as the first immunological reaction or following the washing step. This immunological reagent is provided with a label which is easy to measure. Radioactive substances, chromophores, fluorochromes and luminescence-generating substances are used as label. It is particularly suitable to use as label the indicator enzyme horseradish peroxidase. Peroxidase bound to the test strip acts in an aqueous solution of 4-chloro-1-naphthol, hydrogen peroxide and buffer substance (the latter can, if a test kit with reaction blisters is used, be stored beforehand in one of the reaction blisters 4, 5, 6) to form insoluble 1,4-naphthoquinone, which is immobilized in the test strip. Following another washing step in the siphon blister 1, the proportion of the label immunologically bound to the solid phase is measured.

The test strips may in this case be monoindicators or multiindicators. In the case of monoindicators, the test areas are loaded with the immunological reactant in such a way that only a single analyte from the sample is detected or quantified. Test strips of this type are particularly suitable for detecting and quantifying the total IgE in serum or plasma samples. Multiindicators carry on their various test areas different immunological reactants which react with the appropriate analytes, so that two or more substances can be detected and quantified using this test strip.

The following examples illustrate the invention; the test kit is referred to therein by the name "blister card" used by the laboratory staff.

EXAMPLE 1

Sample from Patient N.N.

Determination of Total IgE Using a Blister Card According to the Invention

The reagents of the total IgE test kit are brought to room temperature (RT=15 to 30° C./30 min), a blister card as shown in FIG. 5*b* is removed and cut open along the lines 3 and 3', and the name of the patient (N.N.) is written on the blister card and an associated patient's card. The total IgE test strip contains the negative control at position 1, the fields for the patient's sample at positions 2 and 3, and the IgE standards 400 kU/l, 100 kU/l, 20 kU/l and 5 kU/l at position 4 to 7.

A pipette is used to introduce 300 μl of patient's serum into the first blister 4 of the blister card, and a dropper bottle is used to add 300 μl of anti-human IgE-peroxidase test solution [(monoclonal mouse) anti-human IgE antibody-peroxidase conjugate (supplied by SBAI, Prod. No. 9160-05) in tris/HCl buffer of pH 7.6 with the addition of 500 ml/l heat-inactivated (56° C./30 min) foetal calf serum, 1 g/l phenol and 0.16 ml/l Kathon 886 WT, 14%)] to the serum which is present. The two solutions are thoroughly mixed by moving the total IgE test strip up and down in the blister several times; the test strip is then incubated in the solution at RT for one hour.

The test strip 2 is then transferred into the siphon blister 1 and washed with distilled water. This entails first rinsing through with distilled water, and then the test strip is incubated in the distilled water at RT for 10 minutes so that the excess (monoclonal mouse) anti-human IgE antibody-peroxidase conjugate can diffuse out of the pores of the nitrocellulose, and then distilled water is rinsed through in the siphon blister once again.

During the washing step (FIGS. 2*a*, 2*b*, 2*c*), chromogen solution [3 g/l 4-chloro-1-naphthol (Fluka, order No. 25328) in analytical grade methanol (Janssen)] is introduced up to the lower mark in the second blister 5 of the blister card, and then "substrate buffer" (11 mmol/l hydrogen peroxide in 10 mmol/l tris/HCl, pH 7.6 with 150 mmol/l NaCl and 0.2 g/l Kathon 886) is added up to the second mark. The test strip 2 is removed from the siphon blister 1 and gently dabbed with a soft paper tissue to remove remaining washing water. The chromogen solution and the substrate buffer solution are thoroughly mixed in the third blister 6 by moving the test strip up and down several times; the test strip is then incubated in this solution at room temperature for 15 minutes.

The test strip 2 is incubated in the siphon blister 1 filled with fresh distilled water at 22° C. for 5 minutes in order to remove the excess chromogen/hydrogen peroxide solution.

The test strip is removed from the siphon blister and gently dabbed with a soft paper tissue to remove remaining liquid.

The dried test strip (after 30 minutes) is placed—in accordance with the instrument instructions—in the densitometer and the colour intensity of the individual coloured spots (dots) is measured.

The measured colour intensity of the two dots with the analytical sample (position 2 and 3) is automatically averaged by the densitometer, and the IgE concentration present in the sample is calculated on the basis of the colour intensity of the IgE standards included.

Result: the serum of patient N.N. contains 20 kU/l IgE.

EXAMPLE 2

Sample from Patient N.N.

Detection of Inhaled Allergen—Specific IgE Using a Blister Card According to the Invention for Serological Diagnosis of an Allergic Disorder:

The reagents of the IgE inhaled allergen test kit are brought to room temperature (22° C./30 min), a blister card as shown in FIG. 5*b* is removed and cut open along lines 3 and 3', and the name of the patient is written on the blister card and an associated patient's card. The test strip for inhaled allergen IgE contains: position 1=negative control, position 2=positive control, position 3=Timothygrass, position 4=artemisia, position 5=ragweed, position 6=rye, position 7=birch, position 8=alternaria, position 9=Dermatophagoides pteronyssinus, position 10=Dermatophagoides farinae, position 11=dog epithelium and position 12=cat epithelium.

A pipette is used to introduce 800 μl of the patient's serum to be investigated into the first blister 4 of the blister card, and test strip 2 is incubated in this patient's serum at RT for four hours.

The test strip 2 is then washed in the siphon blister 1 with distilled water. This entails initial rinsing with distilled water, and then the test strip is incubated in distilled water at RT for 10 minutes so that the unbound material from the patient's serum can diffuse out of the pores of the nitrocellulose. Rinsing through with distilled water is then carried out once again in the siphon blister.

A dropper bottle is used to add anti-human IgE-peroxidase test solution [(monoclonal mouse) anti-human IgE antibody-peroxidase conjugate (supplied by SBAI, Prod. No. 9160-05) in tris/HCl buffer of pH 7.6 with addition of 500 ml/l heat-inactivated (56° C./30 min) foetal calf serum, 1 g/l phenol and 0.16. ml/l Kathon 886 WT, 14%)] up to the upper mark in the second blister 5 of the blister card.

The washed test strip is incubated in blister 5 at 22° C. for one hour.

The test strip 2 is then washed in the siphon blister 1 with distilled water. This entails initial rinsing with distilled water, and then the test strip is incubated in distilled water at RT for 10 minutes so that the unbound material from the patient's serum can diffuse out of the pores of the nitrocellulose. Rinsing through with distilled water is then carried out once again in the siphon blister.

During the washing step, chromogen solution [3 g/l 4-chloro-1-naphthol (Fluka, order No. 25328) in analytical grade methanol (Janssen)] is introduced up to the lower mark in the third blister 6 of the blister card, and then "substrate buffer" (11 mmol/l hydrogen peroxide in 10 mmol/l tris/HCl, pH 7.6 with 150 mmol/l NaCl and 0.2 g/l Kathon 886) is added up to the second mark. The test strip is taken out of the siphon blister and dabbed gently with a soft paper tissue in order to remove remaining washing water. The chromogen solution and the substrate buffer solution are thoroughly mixed in the third blister 6 by moving the test strip up and down several times; the test strip is then incubated in this solution at RT for 15 minutes.

The test strip is incubated with distilled water in the siphon blister at RT for 5 minutes in order to remove excess chromogen.

The test strip is taken out of the siphon blister and dabbed gently with a soft paper tissue in order to remove remaining liquid.

The dried test strip is dried (RT/30 min) and placed—in accordance with the instrument instructions—in the densitometer, and the colour intensity of the individual dots is measured. The RAST classes 0–4 (RAST=RadioAllergoSorbent rest) can be calculated from the measured colour intensities on the various allergen spots with the aid of the colour intensity of the positive control.

Results: The serum of patient N.N. contains:

Timothygrass=RAST class 1

Artemisia=RAST class 0

Ragweed=RAST class 3

Rye=RAST class 1

Birch=RAST class 0

Alternaria=RAST class 0

Dermatophagoides pteronyssinus=RAST class 0

Dermatophagoides farinae =RAST class 0

Dog epithelium=RAST class 1

Cat epithelium=RAST class 4

EXAMPLE 3

Sample from Patient N.N.

Detection of Food Allergen—Specific IgE Using a Blister Card According to the Invention for Serological Diagnosis of an Allergic Disorder:

The reagents of the IgE food allergen test kit are brought to room temperature (RT/30 min), a blister card as shown in FIG. 5*b* is removed and cut open along lines 3 and 3', and the name of the patient is written on the blister card and an associated patient's card. The test strip for food allergen IgE contains: position 1=negative control, position 2=positive control, position 3=wheat, position 4=soya beans, position 5=maize, position 6=hazelnut, position 7=peanut, position 8=milk, position 9=egg, position 10=cod, position 11=tomato and position 12=orange.

A pipette is used to introduce 800 μl of the patient's serum to be investigated into the first blister 4 of the blister card; the test strip 2 is then incubated in this patient's serum at RT for four hours.

The test strip 2 is then washed in the siphon blister 1 with distilled water. This entails initial rinsing with distilled water, and then the test strip is incubated in distilled water at RT for 10 minutes so that the unbound material from the patient's serum can diffuse out of the pores of the nitrocellulose. Rinsing through with distilled water is then carried out once again in the siphon blister.

A dropper bottle is used to add anti-human IgE-peroxidase test solution [(monoclonal mouse) anti-human IgE antibody-peroxidase conjugate (supplied by SBAI, Prod. No. 9160-05) in tris/HCl buffer of pH 7.6 with addition of 500 ml/l heat-inactivated (56° C./30 min) foetal calf serum, 1 g/l phenol and 0.16 ml/l Kathon 886 WT, 14%)] up to the upper mark in the second blister 5 of the blister card. The washed test strip is removed from the siphon blister and incubated in blister 5 at RT for one hour.

The test strip is then transferred anew into siphon blister 1 and washed with distilled water. This entails first rinsing through with distilled water, and then the test strip is incubated in distilled water at RT for 10 minutes so that the excess (monoclonal mouse) anti-human IgE antibody-peroxidase conjugate can diffuse out of the pores of the nitrocellulose, and then rinsing through with distilled water is carried out once again.

During the washing step, chromogen solution [3 g/l 4-chloro-1-naphthol (Fluka, order No. 25328) in analytical grade methanol (Janssen)] is introduced up to the lower mark in the third blister 6 of the blister card, and then "substrate buffer" (11 mmol/l hydrogen peroxide in 10 mmol/l tris/HCl, pH 7.6 with 150 mmol/l NaCl and 0.2 g/l Kathon 886) is added up to the second mark. The test strip is taken out of the siphon blister 1 and dabbed gently with a soft paper tissue in order to remove remaining washing water. The chromogen solution and the substrate buffer solution are thoroughly mixed in the third blister 6 by moving the test strip up and down several times; the test strip is then incubated in this solution at RT for 15 minutes.

The test strip is incubated in the siphon blister filled with fresh distilled water at 22° C. for 5 minutes in order to remove excess chromogen.

The test strip is removed from the siphon blister and dabbed gently with a soft paper tissue to remove remaining liquid.

The test strip is dried (RT/30 min) and placed—in accordance with the instrument instructions—in the densitometer, and the colour intensity of the individual dots is measured. RAST classes 0–4 can be calculated from the measured colour intensities on the various allergen spots with the aid of the colour intensity of the positive control.

Results: The serum of patient N.N. contains:

Wheat=RAST class 2

Soya beans=RAST class 2

Maize=RAST class 1

Hazelnut=RAST class 2

Peanut=RAST class 3

Milk=RAST class 0

Egg=RAST class 0

Cod=RAST class 0

Tomato=RAST class 1

Orange=RAST class 1

What is claimed is:

1. A test kit for carrying out analytical tests, the test kit comprising a water-impermeable substrate and, bonded or welded thereto, a transparent plastic sheet including blisters arranged parallel to one another, wherein at least one blister includes an elongate container having an S-shaped part and a rinsing part connected to the elongate container by the S-shaped part, the elongate container and the rinsing part together functioning as a siphon.

2. The test kit according to claim 1, wherein at least one of the blisters contains a test strip.

3. The test kit according to claim 2, wherein the blister including the elongate container and the rinsing part includes, adjoining the container, a removal part having a cross-sectional area larger than a cross-sectional area of the container part.

4. The test kit according to claim 2, wherein the blisters not functioning as a siphon comprise an elongate reaction part and a funnel-shaped introduction part having a cross-sectional area larger than a cross-sectional area of the reaction part.

5. The test kit according to claim 4, wherein the removal part of the blister functioning as a siphon and the introduction part are side by side and can be cut through along a single straight line.

6. The test kit according to claim 5, including a preperforated line along the single straight line to facilitate cutting.

7. The test kit according to claim 1, including volumetric measurement scales beside or on each of the blisters not functioning as a siphon, in the region of the reaction part.

8. The test kit according to claim 2, wherein the test strip has a test area loaded with an immunological reactant for detection or quantification of total IgE, of an IgE specific for an inhaled allergen, or of an IgE specific for a food allergen.

9. The test kit according to claim 1, wherein the sheet is a plastic which is hydrophobic or has been made hydrophobic.

10. Use of the test kit according to claim 1, for carrying out an ELISA test.

11. The test kit according to claim 3, wherein the blisters not functioning as a siphon comprise an elongate reaction part and a funnel-shaped introduction part having a cross-sectional area larger than a cross-sectional area of the reaction part.

12. The test kit according to claim 11, wherein the removal part of the blister functioning as a siphon and the introduction part are side by side and can be cut through along a single straight line.

13. The test kit according to claim 12, further including a preperforated line along the single straight line to facilitate cutting.

14. The test kit according to claim 3, including volumetric measurement scales beside or on each of the blisters not functioning as a siphon, in the region of the reaction part.

15. The test kit according to claim 4, including volumetric measurement scales beside or on each of the blisters not function as a siphon, in the region of the reaction part.

16. The test kit according to claim 5, further including volumetric measurement scales beside or on each of the blisters not functioning as a siphon, in the region of the reaction part.

17. The test kit according to claim 3, wherein the test strip has a test area loaded with an immunological reactant for detection or quantification of total IgE, of an IgE specific for an inhaled allergen, or of an IgE specific for a food allergen.

18. The test kit according to claim 4, wherein the test strip has a test area loaded with an immunological reactant for detection or quantification of total IgE, of an IgE specific for an inhaled allergen, or of an IgE specific for a food allergen.

19. The test kit according to claim 3, wherein the sheet is a plastic which is hydrophobic or has been made hydrophobic.

20. The test kit according to claim 4, wherein the sheet is a plastic which is hydrophobic or has been made hydrophobic.

* * * * *